United States Patent [19]

Glotin et al.

[11] Patent Number: 4,782,695
[45] Date of Patent: Nov. 8, 1988

[54] METHOD AND APPARATUS FOR MEASURING THE BUBBLE POINT OF OIL IN AN UNDERGROUND FORMATION

[75] Inventors: Bernard J. P. Glotin, Saint Maur; Jacques P. Exbraynt, Milan, both of France

[73] Assignee: Schlumberger Technology Corporation, Houston, Tex.

[21] Appl. No.: 910,038

[22] Filed: Sep. 22, 1986

[30] Foreign Application Priority Data

Sep. 23, 1985 [FR] France ............................ 85 14060

[51] Int. Cl.⁴ ............................................. E21B 49/10
[52] U.S. Cl. ...................................................... 73/155
[58] Field of Search .................. 73/151, 155, 38, 61 R, 73/19; 166/250

[56] References Cited

U.S. PATENT DOCUMENTS

| | | | |
|---|---|---|---|
| 2,138,141 | 11/1938 | Cromer et al. | 73/19 |
| 3,937,060 | 2/1976 | Lewis et al. | 73/19 |
| 4,210,025 | 7/1980 | Bimond et al. | 73/155 X |
| 4,583,595 | 4/1986 | Czernichow et al. | 166/264 |

FOREIGN PATENT DOCUMENTS

| | | | |
|---|---|---|---|
| 0129584 | 12/1959 | U.S.S.R. | 73/155 |
| 0341927 | 7/1972 | U.S.S.R. | 73/151 |

Primary Examiner—Jerry W. Myracle
Attorney, Agent, or Firm—Henry N. Garrana

[57] ABSTRACT

The invention relates to measuring the bubble point of oil down a well drilled into an underground formation. The pressure is measured by an apparatus lowered down the well. The apparatus comprises a chamber (2) in which a small quantity of oil is confined in a volume which is variable by a needle (3) having portions of different diameters (3a, 3b) capable of being inserted to a greater or lesser extent into the chamber (2) under drive from a motor (7). Values of pressure inside the chamber and of chamber volume are respectively measured by a manometer (11) and by a displacement sensor (12) connected to the needle (3) and are transmitted to the surface.

9 Claims, 7 Drawing Sheets

METHOD AND APPARATUS FOR MEASURING THE BUBBLE POINT OF OIL IN AN UNDERGROUND FORMATION

The present invention relates to measuring the bubble point of oil in an underground formation into which a well has been drilled.

BACKGROUND OF THE INVENTION

It is conventional to investigate the characteristics of oil contained in an underground formation by taking samples and raising them to the surface. However, in order to ensure that oil taken in this way from a well retains the properties which it has at a distance from the well in said formation, it is necessary for the oil to be in a single phase condition at the point where a sample is taken. Otherwise, the samples obtained are not representative of the bulk of the oil in the formation.

Generally, the single phase state of the oil being sampled in a well is verified by measuring the bubble point of sample raised to the surface, i.e. by measuring the pressure above which the gases mixed with the oil are completely dissolved in the oil so that the oil behaves as a single phase liquid. Given the pressure and the temperature down the well where the sample is taken, it is possible to deduce whether the oil at that location is indeed in a single phase state. Performing such a bubble point measurement in the laboratory requires the oil to be re-compressed to a pressure of the same order as the down-hole pressure, and also requires the oil to be heated to the temperature of the underground formation.

This type of measurement therefore requires lengthy operations and the results indicating whether or not the samples obtained are valid are obtained only a considerable length of time after the samples were taken, and in some cases that may mean that it is already too late to take new samples.

Preferred implementations of the present invention avoid the above drawbacks by performing bubble point measurements rapidly and down-hole, thereby enabling the validity or otherwise of samples being taken to be established on site and in good time.

SUMMARY OF THE INVENTION

The present invention provides a method of measuring the bubble point of oil in an underground formation into which a well has been drilled, the method consisting essentially in:

lowering a tool down the well, said tool including a chamber whose volume is variable on command;

opening the chamber so that it fills with oil;

closing the chamber and causing its volume to vary gradually while measuring the pressure P inside the chamber for each value of volume V imposed thereon;

establishing the curve $P = f(V)$ from the measurement points obtained in this way; and deducing the bubble point from said curve.

Preferably, in order to obtain accurate measurements even when the bubble point pressure is close to the down-hole pressure, the method begins, once the chamber full of oil has been closed, by reducing the volume of the chamber so as to increase the pressure therein relative to the ambient pressure of oil in the well; and the continues by increasing the volume of the chamber in stages with successive values of volume and pressure being taken in order to establish said curve.

The invention also provides apparatus for measuring the bubble point of oil in an underground formation into which a well has been drilled, said apparatus being constituted by a tool designed to be lowered down the well and comprising:

a rigid-walled chamber having at least one orifice through said wall;

a needle insertable through at least said one orifice to vary the volume of said chamber;

drive means for driving said needle in longitudinal translation;

a manometer for measuring the pressure P inside said chamber; and a displacement sensor coupled to said needle;

said chamber being capable of being opened for filling with oil and said manometer and said displacement sensor delivering signals enabling the bubble point of said oil to be determined.

These signals may either be transmitted to the well head, for example by means of an electric cable, or else they may be stored in a memory down-hole, which memory may subsequently be raised by a mere mechanical cable in order to be read at the surface.

In a preferred embodiment, the needle comprises two successive portions of different cross-section, namely a first portion which is extended by means of a second portion of smaller cross-section than the first, and wherein said chamber includes two aligned orifices enabling said needle to pass right through said chamber, namely a first orifice complementary in section to said first needle portion and a second orifice complementary in section to said second needle portion, said orifices being closed by respective ones of said needle portions when said needle is caused to pass through said chamber. It will be understood that in this case the chamber is completely isolated from the surrounding medium and that the small quantity of oil confined therein is subjected to pressure variations which result from the variations in volume created by the movement of the needle, with the volume being offered to the oil depending on the variable ratio between the respective lengths of the first and second portions of the needle to be found inside the chamber. In contrast, when the needle drive means withdraw it completely from the chamber, thereby opening its orifice of orifices, the chamber is put into communication with the outside medium and therefore fills with oil.

As a safety precaution and in order to avoid any damage to the equipment, it is desirable to provide a first (and preferably also a second) pressure release valve for limiting the pressure between the inside volume of the chamber and the outside medium, the first and second valves serving to provide relief when the pressure in the chamber becomes respectively too high or too low relative to the pressure in the well due to movements of the needle.

The needle drive means may comprise an electric motor housed in a housing which is pressure-proof, with a threaded rod being rotated by the motor through the wall of its housing by means of a magnetic coupling device, and with a nut mounted on the threaded rod and fixed to the needle, thereby moving the needle in longitudinal translation when the motor causes the threaded rod to rotate. The displacement sensor for measuring needle movement may be constituted by a linear potentiometer.

When the orifice of said chamber which co-operates with said second portion of the needle is provided with an annular sealing ring, it is preferable, in order to avoid any damage to or loss of said seal when the chamber is re-opened to the surrounding medium via said orifice, to provide a pressure-equalizing duct passing through the end of the needle to put the chamber into communication with the surrounding medium when the needle is about to leave said orifice as it is being withdrawn from the chamber, but while the end of the needle is still engaged inside the sealing ring.

The above-defined invention is used directly in the well to obtain a good approximation to the bubble point of the oil in the well, thereby making it possible to establish whether any oil samples being taken in the well are valid and also providing the benefit of the sample quality control directly on site. If for some reason a sample is not valid, a new sampletaking operation and the associated operation of checking whether the sample is valid may be performed while the measuring apparatus is still in the well.

BRIEF DESCRIPTION OF THE DRAWINGS

An embodiment of the invention is described by way of nonlimiting example with reference to the accompanying drawings, in which.

MORE DETAILED DESCRIPTION

Figure 1:
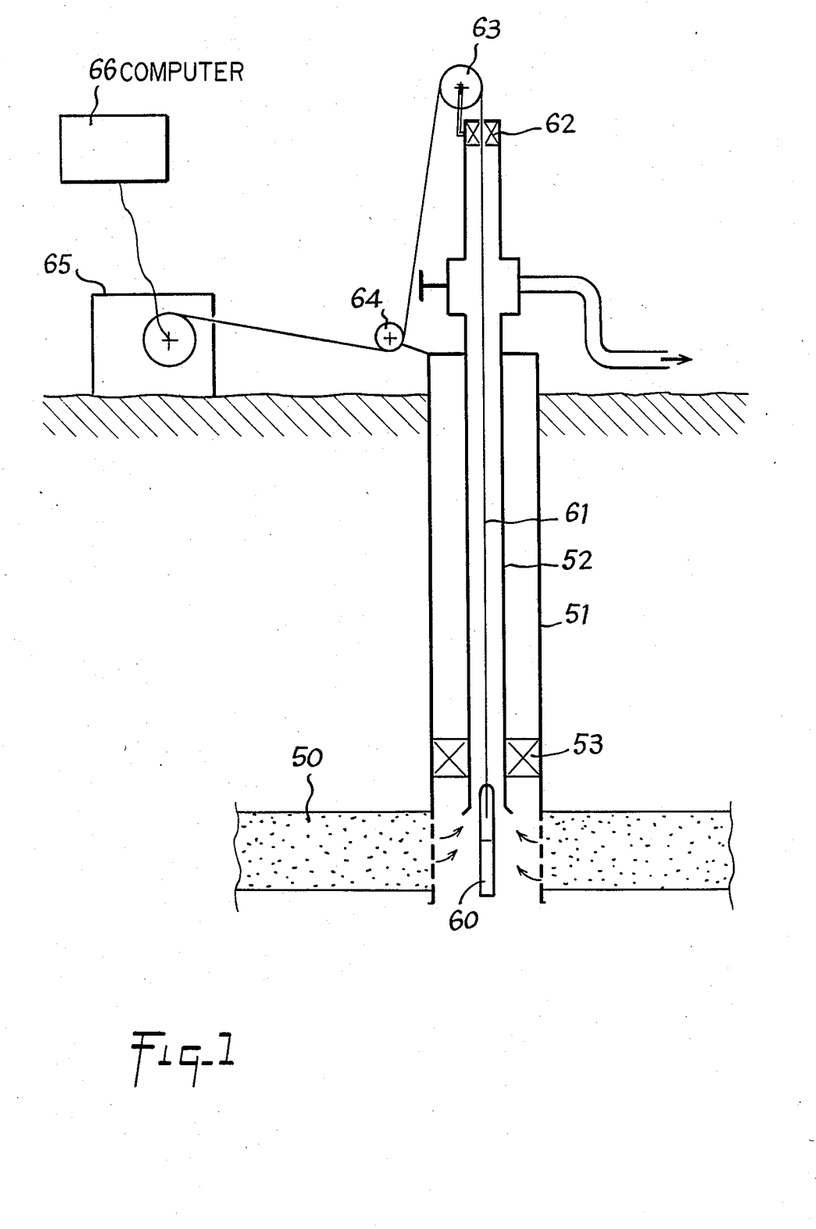
FIG. 1 is a diagrammatic vertical section through an oil well down which measuring apparatus in accordance with the invention has been lowered.

FIG. 1 shows a well drilled in a oil-producing zone 50 and comprising a production column 52 in casing 51. An annular sealing device 53 is placed between the bottom of the production column and the casing 51. Measuring apparatus 60 in accordance with the invention is lowered to the level of the productive zone 50 by means of a cable 61 from which it is suspended. The cable passes inside the production column 52 and emerges from the top thereof through a sealing device 62 and is then guided by pulleys 63 and 64 to be wound onto the drum of a winch 65 disposed on the ground. The cable 61 is an electric cable which, in addition to providing the mechanical function of suspending the measuring apparatus 60, also provides the function of transmitting measurement signals to the surface and of transmitting control signals to the apparatus 60, and also to other devices which may be associated therewith, for example sampling volumes whose operation is controlled from the surface. These signals are controlled by a computer 66 which constitutes a controlling and recording unit.

Figures 2, 3:
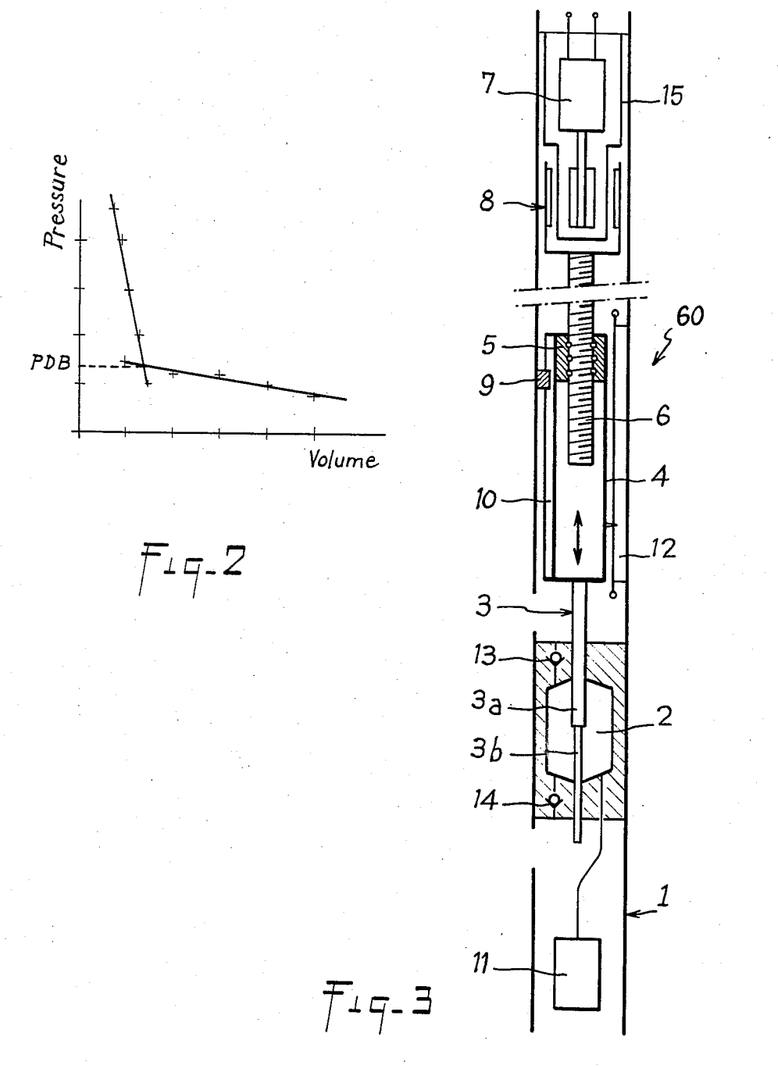
FIG. 2 is a graph showing a pressure/volume curve for determining the bubble point of a liquid/gas mixture.
FIG. 3 is a simplified diagram of the structure of measuring apparatus in accordance with the invention.

Operation of the measuring apparatus 60 is based on the FIG. 2 graph which shows pressure variations as a function of the volume of a liquid/gas mixture, the gas being soluble to some extent in the liquid. When high pressure is applied to the mixture, a given pressure variation gives rise to a small variation in the volume of the mixture. However, if the pressure drops below a value PDB, bubbles of gas appear in the mixture and the volume varies to a much greater extent for the same pressure variation. The pressure PDB is the "bubble point" above which the mixture is completely liquid and does not include any fraction in the gaseous state.

The apparatus described below is intended for measuring the bubble point of a mixture of hydrocarbon and gas, and this measurement is to be performed down a well drilled into an underground formation, prior to taking a sample of the fluid mixture.

With reference to FIG. 3, the apparatus is essentially constituted by a circularly cylindrical elongate envelope 1, a thick-walled chamber 2, a needle 3 having two portions 3a and 3b of different diameters and capable of being inserted into the chamber 2, said needle being capable of being driven in longitudinal translation by a mechanism comprising a cylindrical part 4 having the needle 3 fixed to one end thereof and having its other end fixed to a nut 5 which is mounted on a threaded rod 6 rotated by an electric motor 7 housed in a pressure-proof housing 15. The motor drives the rod through the housing wall by means of a magnetic coupling 8. Above the motor 7 there is an electronic control portion for the tool, together with a connector enabling the apparatus to be connected either directly to an electric cable going up to the surface, or else to some other device. When the motor 7 is switched on to rotate in one direction or the other, it rotates the threaded rod 6 and thereby causes the nut 5 to move longitudinally along the rod, thus causing the cylindrical part 4 to move in translation since the part 4 is prevented from rotating by a fixed peg 9 engaged in a rectilinear guide groove 10 made in the part 4. In turn, the part 4 causes the needle 3 to move into or out from the chamber 2 depending on the direction of rotation of the motor 7. The inside volume of the chamber 2 varies depending on the degree to which the larger diameter portion 3a of the needle 3 is engaged therein, thereby subjecting the fluid contained in the chamber to pressure variations which are measured by means of a manometer 11. The volume of the chamber 2 can be deduced from the longitudinal position of the part 4 which drives the needle 3, and this position is measured by means of a linear potentiometer 12 which measures displacements of said part relative to the envelope 1 of the apparatus.

The apparatus also includes a temperature probe for measuring the temperature of the oil in the well. The values measured by this probe are transmitted to the surface, as are the values delivered by the manometer 11 and the potentiometer 12.

The main stages of measuring the bubble point are now described with reference to FIGS. 4a to 4d.

Initially (FIG. 4a) the needle 3 is completely withdrawn from the chamber 2, thereby opening orifices 2a and 2b which are disposed in alignment through the wall of the chamber 2 in order to allow the needle to pass therethrough. The fluid to be measured can thus pass freely through the chamber 2 either by virtue of natural fluid flow around the apparatus, or else by moving the apparatus vertically along the well down which it has been lowered. The chamber 2 is thus filled with a small quantity of fluid at the pressure P1 in the well at that depth.

The motor 7 is switched on to cause the needle 3 to penetrate into the chamber 2. The orifices 2a and 2b have diameters equal to the diameters of the portions 3a and 3b respectively of the needle, and they are therefore closed in sealed manner by said needle portions. The fluid present in the chamber 2 is thus confined in a certain volume. As the needle 3 continues its motion, its larger diameter portion 3a penetrates further into the chamber and thus reduces the volume available to the fluid inside the chamber (FIG. 4b), thereby subjecting the fluid to increasing pressure, greater than the pressure P1. The value of this pressure is limited to a maximum value $P2=P1+\Delta P$ by a pressure release valve 13 connected between the inside volume of the chamber 2 and the surrounding space at pressure P1.

Figure 4A:
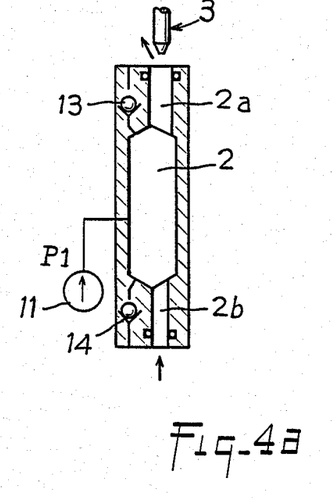
FIGS. 4a to 4d are diagrams showing successive stages in a bubble point measuring operation performed in accordance with the invention.
Figure 4B:
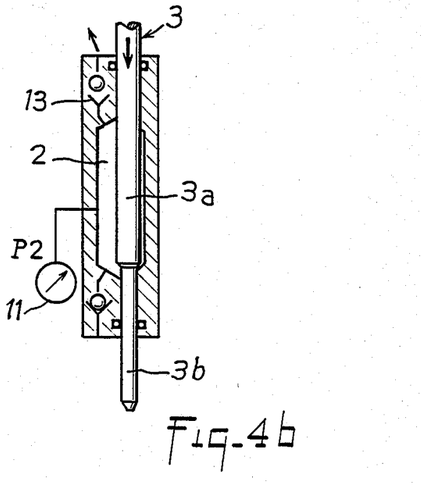
Figure 4C:
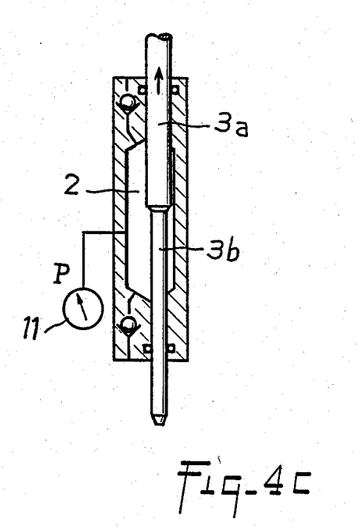
Figure 4D:
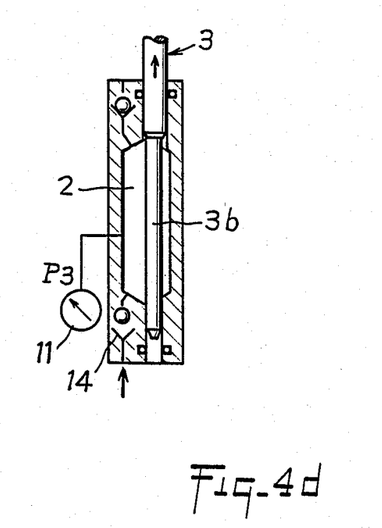
Figures 5, 6:
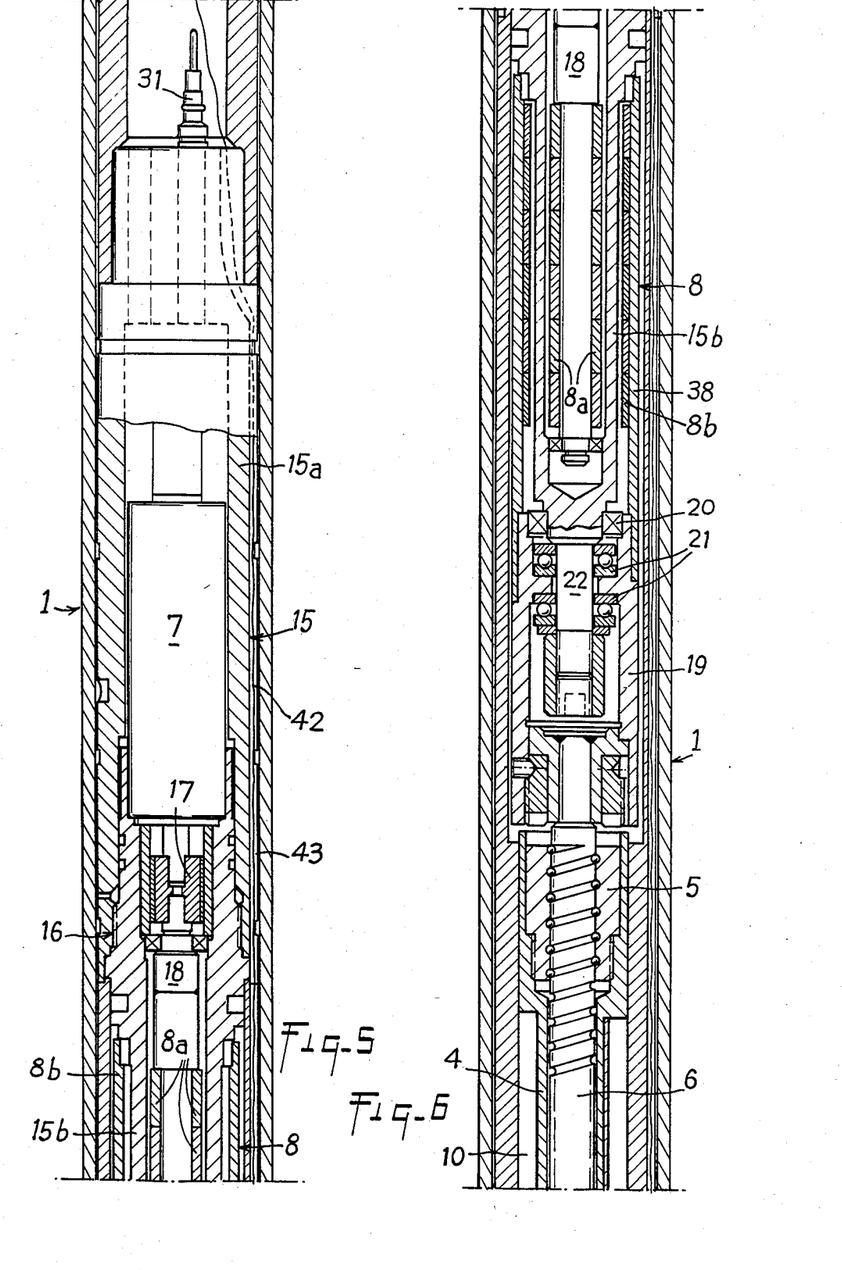
FIGS. 5 to 9 are longitudinal section through various portions of apparatus in accordance with the invention, said sections being taken at different points along the length of a specific embodiment.

Once the needle 3 has reached its position of maximum insertion, with the chamber 2 being almost exclusively occupied by its larger diameter portion 3a, the motor 7 is stopped and then stepped in the opposite direction so as to extract needle 3 in stages, thereby gradually increasing the volume of the chamber 2 with the large diameter portion 3a of the needle giving place step-by-step to the smaller diameter portion 3b. However, the smaller diameter portion is nevertheless long enough to ensure that the orifice 2b through which it passes remains closed, and that this continues substantially up to the moment when the larger diameter portion 3a has completely left the chamber 2. As a result, the pressure P of fluid drops off, and it continues to be measured by the manometer 11 while the increasing volume of the chamber is determined by the position of the needle 3 as measured by the potentiometer 12. The pressure P drops in this manner to a value whose lower limit is set by a second pressure release valve 14 disposed similarly to the valve 13, but in the opposite direction so that the minimum pressure $P3=P1-\Delta P'$ which is less than the pressure P1, but is not too far removed therefrom.

FIGS. 5 to 9 show a concrete embodiment of apparatus in accordance with the invention. These figures show the internal structure of successive portions of the apparatus, which portions follow one another in the same order as the figure numbers starting from the top end and going downwards when the apparatus is located in the production column of an oil well.

These figures show:

the motor 7 in its pressure-proof housing 15 which is constituted by two portions 15a and 15b screwed together at 16, with the portion 15a including sealed electrical feed-throughs 31 for powering the motor;

the magnetic coupling device 8 which comprises a central shaft 18 driven by the motor 7 via a flexible link 17 and carrying magnets 8a, with the tubular metal element 38 disposed coaxially around the shaft 18, outside the housing 15 and carrying magnets 8b. The housing 15 is made of a non-magnetic alloy so that the magnetic fields of the magnets 8a and 8b pass through the housing and transmit mechanical force from the shaft 18 to the element 38. The element 38 is extended by means of a tubular bearing part 19 which is guided to rotate without any possibility of axial translation relative to the general axis of the apparatus by means of a ball bearing 20 and by means of ball abutments 21 mounted on a short shaft 22 fixed to the housing 15;

the threaded rod 6 which is fixed to the tubular element 38 by means of the bearing part 19;

the nut 5 which is a ball nut mounted on the threaded rod 6;

the cylindrical part 4 which is fixed to the nut 5 and which is driven in translation thereby along the longitudinal axis of the apparatus, and which is prevented from rotating by means of its guided groove 10 having the fixed peg 9 engaged therein;

the needle 3 which is fixed to the part 4 and which has two portions 3a and 3b of different diameters;

the chamber 2 capable of receiving the needle 3 and having it pass therethrough via orifices 2a and 2b fitted with sealing rings 23 and 24 and having respective diameters matching the diameters of the portions 3a and 3b of the needle 3; and the manometer 11 which is connected via a duct 30 and a capillary tube 25 to the chamber 2, said tube being filled with an inert fluid for protecting the internal components of the manometer.

The inside space of the apparatus which extends between the sealed electric feed-throughs 31 situated above the motor 7 (FIG. 5) and sealed electric feed-throughs provided in a zone 39 situated at the other end of the apparatus (FIG. 9) is filled with an insulating fluid (mineral oil). In conventional manner, this fluid is maintained at substantially the same pressure as the fluid in the well by means of a floating piston 40 (FIG. 7) which separates the well fluid from the insulating fluid inside the apparatus. The separating piston 40 has the needle 3 passing therethrough and is urged by a spring 41 so as to maintain the insulating oil inside the apparatus at a slightly higher pressure than the surroundings. This allows the apparatus to operate in a high pressure environment which contains fluids that may be corrosive and/or conductive.

Figures 7, 10, 11:
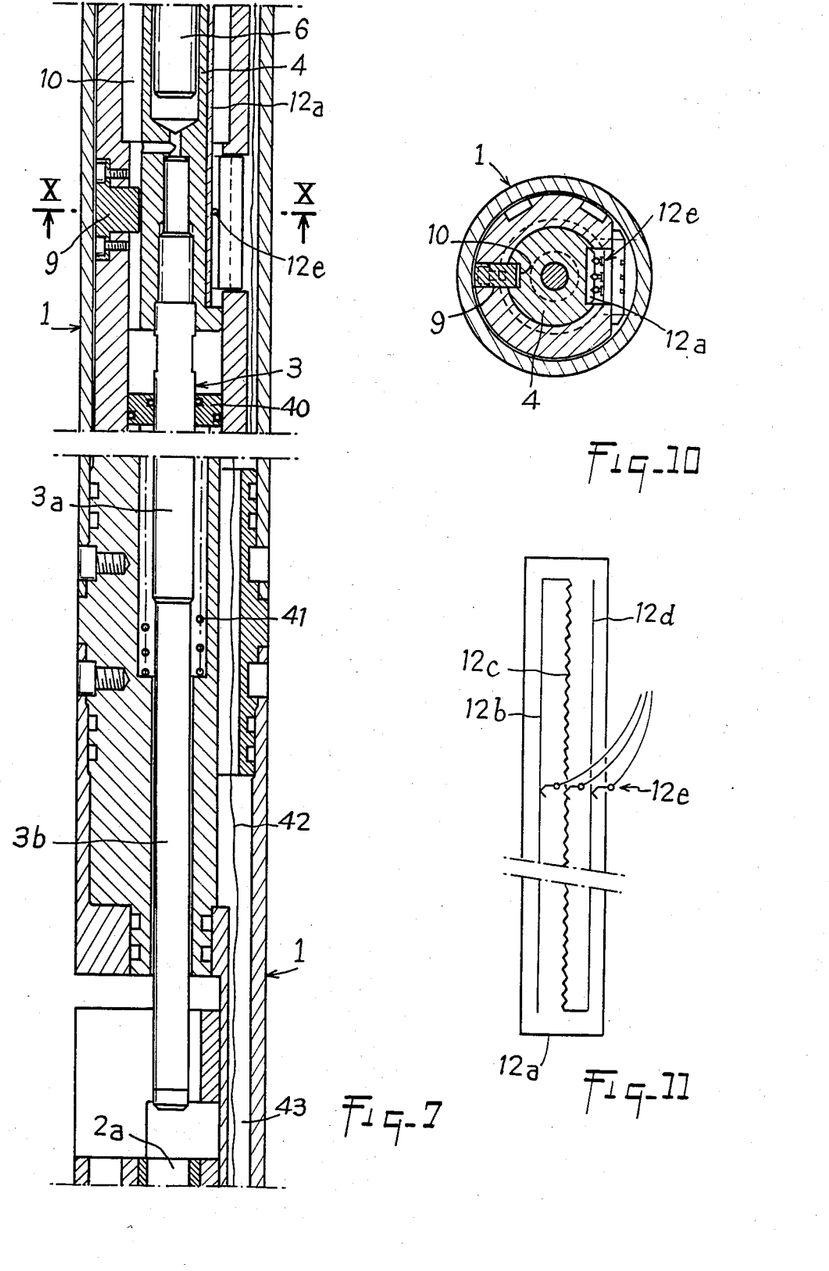
FIG. 10 is a cross-section on line X—X of FIG. 7.
FIG. 11 is a diagram showing the configuration of a linear potentiometer constituting a displacment sensor.

As shown in FIGS. 10 and 11, the potentiometer 12 comprises a plane support 12a of insulating material mounted longitudinally on the part 4 with three rectilinear electrically conductive tracks 12b, 12c, and 12d disposed geometrically in parallel and electrically in series, thereon. The end tracks 12b and 12d are of substantially zero resistance and the intermediate track 12c constitutes the resistive track of the poteniometer. A set of three fixed brushes 12e rub against these tracks and constitute the three terminals of the potentiometer 12.

Figures 8, 9:
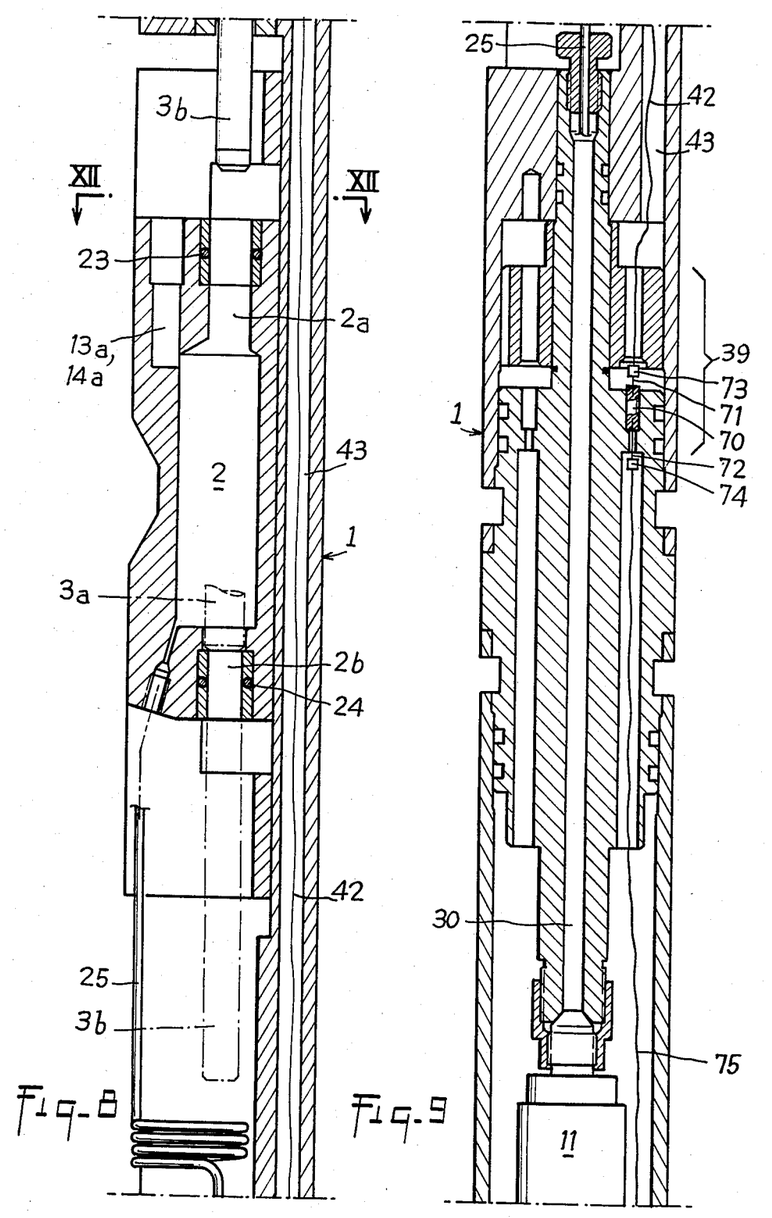
Figure 12:
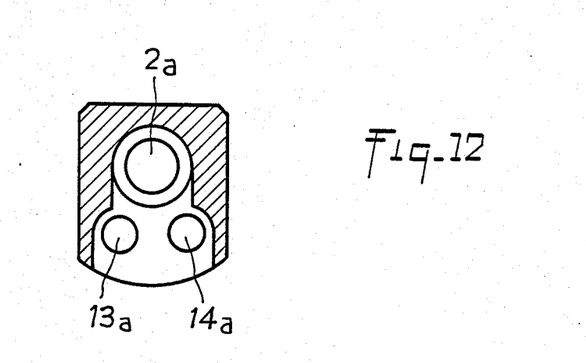
FIG. 12 is a cross-section on a line XII—XII of FIG. 8.

Also, FIGS. 8 and 12 show that the two pressure release valves 13 and 14 capable of putting the inside of the chamber 2 into communication with the surrounding medium are disposed on the same side of said chamber in recesses 13a and 14a provided side-by-side in one of the ends of the chamber wall.

Figure 13:
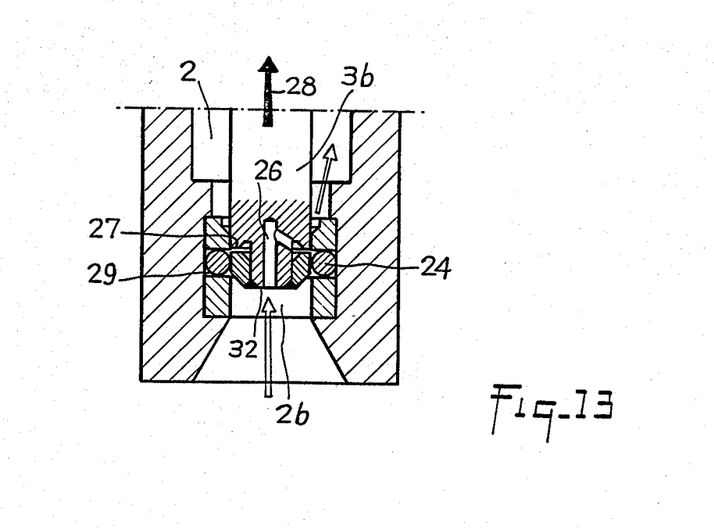
FIG. 13 is a longitudinal section through the end of the moving needle of the apparatus showing the pressure-equalizing duct, and drawn to a slightly larger scale.

FIG. 13 shows the end structure of the end portion 3b of the needle 3. It can be seen that a channel 26 is provided in said end, and is open firstly to the front face 32 at the leading end of the needle and secondly to a peripheral groove 27 provided in the side surface of the needle at a distance from its front face 32, which distance is slightly greater than the thickness of the seal 24. This arrangement serves, when the needle is about to leave the orifice 2b of the chamber 2 in the direction of arrow 28 when the pressure P3 inside the chamber is less than the surrounding pressure P1, to connect the chamber to the surrounding medium by means of a path (groove 27 and channel 26) which passes round the seal 24 while the sealing ring is itself still held in place the needle. Thus, there is no risk of the sealing ring being damaged or ejected by a sudden rush fluid between pressure values P3 and P1.

A bundle of electric connection wires 42 passes along the device from end to end via a tunnel 43 provided in its envelope 1. The sealed feed-through of the zone 39 (see FIG. 9) comprises a sealed feed-through per se 70 terminated at each end by pins 71 and 72 connected to respective sockets 73 and 74. The end 75 of the bundle of electric wires 42 is connected to the electrical portion (not shown) of the pressure sensor 11, situated beneath said sensor. The chamber 2 is made in the form of an independent component with the tunnel 43 running past the side thereof (see FIG. 8). It is easily detached from the envelope 1 in order to give access to the sealing rings 24 and without requiring the bundle of electric wires 42 passing through the device to be removed as well.

By way of indication, the following technical specifications apply to a particular embodiment of apparatus in accordance with the above description:

overall length of device: 2.75 m;

pressure and temperature which can be withstood in a well: about 1050 bar and 175° C.;

volume of the chamber 2: 12 cm$^3$;

maximum variation in the volume of the chamber 2: 10%;

diameters of the portions 3a and 3b of needle, respectively: 9 and 7.8 mm, giving a variation in chamber volume 13.5 mm$^3$ per mm of needle displacement;

maximum variation of the pressure inside the chamber 2 relative to the surrounding medium: about ±210 bar; and range of pressures measured by the manometer 11: about 700 or 1400 bar.

It should be observed that an apparatus of the type described above is designed for measuring bubble point characteristics of oil solely down-hole, and it is not suitable for raising to the surface samples of oil taken down the well. Thus, it needs to be associated, in practice, with at least one sampler in a set of multiple tools.

Further, it may be observed that a device in accordance with the invention can be used for performing repeated measurements as often as desired throughout the production period of the well.

We claim:

1. A method of measuring the bubble point of oil in an underground formation into which a well has been drilled, the method comprising the steps of:
   lowering a tool down the well, said tool including a chamber whose volume is variable on command;
   opening the chamber so that it fills with oil;
   closing the chamber and causing its volume to vary while measuring the pressure P inside the chamber for each value of volume V imposed thereon, said variation of the volume being initially a reduction so as to make the pressure in the chamber greater than the ambient pressure of the well, and said reduction being followed by gradual increases;
   establishing the curve P=f(V) from the measurement points obtained in this way; and
   deducing the bubble point from said curve.

2. Apparatus for measuring the bubble point of oil in an underground formation into which a well has been drilled, said apparatus being constituted by a tool designed to be lowered down the well and comprising:
   a rigid-walled chamber having at least one orifice through said wall;
   a needle insertable through at least said one orifice to vary the volume of said chamber;
   drive means for driving said needle in longitudinal translation;
   a manometer for measuring the pressure P inside said chamber; and
   a displacement sensor coupled to said needle;
   said chamber being capable of being opened for filling with oil and said manometer and said displacement sensor delivering signals enabling the bubble point of said oil to be determined.

3. Apparatus according to claim 2, wherein said needle comprises two successive portions of different cross-section, namely a first portion which is extended by means of a second portion of smaller cross-section than the first, and wherein said chamber includes two aligned orifices enabling said needle to pass right through said chamber, namely a first orifice complementary in section to said first needle portion and a second orifice complementary in section to said second needle portion, said orifices being closed by respective ones of said needle portions when said needle is caused to pass through said chamber.

4. Apparatus according to claim 3, wherein the orifice of said chamber which co-operates with said second portion of the needle is provided with an annular sealing ring, and wherein the end of said needle has a pressure-equalizing duct passing therethrough to put the chamber into communication with the surrounding medium when the needle is about to leave said orifice as it is being withdrawn from the chamber but while the end of the needle is still engaged inside the sealing ring.

5. Apparatus according to claim 2, wherein said needle drive means is suitable for withdrawing the needle sufficiently from said chamber to open the, or each, orifice therethrough, thereby enabling the chamber to be filled with oil.

6. Apparatus according to claim 2, wherein a first pressure release valve is disposed between the inside volume of the chamber and the surrounding medium, said valve being disposed to limit the amount by which the pressure inside said chamber may rise above the pressure P1 in the well.

7. Apparatus according to claim 6, including a second pressure release valve is disposed between the inside volume of the chamber and the surrounding medium, said valve being disposed to limit the amount by which the pressure inside said chamber may fall below the pressure P1 in the well.

8. A device according to claim 2, wherein said needle drive means comprise an electric motor housed in a pressure-proof housing, a threaded rod rotated by the motor through the wall of said housing by means of a magnetic coupling, and a nut mounted on the threaded rod and fixed to the needle.

9. Apparatus according to claim 2, wherein the needle displacement sensor is constituted by a linear potentiometer.

* * * * *